United States Patent
Horan et al.

(10) Patent No.: US 6,623,974 B1
(45) Date of Patent: Sep. 23, 2003

(54) METHOD AND APPARATUS FOR THE ANALYSIS OF A LIQUID CARRYING A SUSPENSION OF ORGANIC MATTER

(75) Inventors: Martin Horan, Cork (IE); Seamus O'Mahony, Cork (IE)

(73) Assignee: Analytical Developments Limited, County Cork (IL)

( * ) Notice: Subject to any disclaimer, the term of this patent is extended or adjusted under 35 U.S.C. 154(b) by 0 days.

(21) Appl. No.: 09/532,459

(22) Filed: Mar. 23, 2000

(30) Foreign Application Priority Data

Mar. 23, 1999 (IE) ............................................. S990232

(51) Int. Cl.$^7$ ............................................. G01N 33/00
(52) U.S. Cl. .................... 436/135; 436/131; 436/133; 436/145; 436/146; 436/160
(58) Field of Search ........................... 436/131, 133, 436/135, 145, 146, 155, 160

(56) References Cited

U.S. PATENT DOCUMENTS

| | | | |
|---|---|---|---|
| 3,958,941 A | * 5/1976 | Regan | 23/253 |
| 4,101,783 A | 7/1978 | Hutter | 250/540 |
| 4,619,902 A | * 10/1986 | Bernard | 436/145 |
| 5,034,198 A | 7/1991 | Kaiga et al. | 422/186 |
| 5,132,094 A | * 7/1992 | Godec et al. | 422/68.1 |
| 5,324,666 A | * 6/1994 | Siepmann et al. | 436/62 |
| 5,733,789 A | * 3/1998 | Wright et al. | 436/146 |

FOREIGN PATENT DOCUMENTS

| | | |
|---|---|---|
| DE | 2540855 | 3/1977 |
| GB | 2048029 | 12/1980 |

* cited by examiner

*Primary Examiner*—Jan Ludlow
*Assistant Examiner*—Sam P. Siefke
(74) *Attorney, Agent, or Firm*—Jacobson Holman PLLC

(57) ABSTRACT

The invention provides an ozone hydroxy radical analysis method for a liquid carrying a suspension of organic matter. The analyser includes a reactor vessel 2 having sample inlets and outlets 3 and 4 respectively for a liquid stream 5. The reactor vessel 2 is connected to a control system 10 and is fed from an acid vessel 15, a base vessel 16 and an ozone generator 20. The reactor vessel 2 contains glass beads and a catalyst is introduced into the reactor vessel. With a manganese catalyst and glass beads, the manganese coats the glass beads which therefore retain catalyst with the reactor vessel.

43 Claims, 9 Drawing Sheets

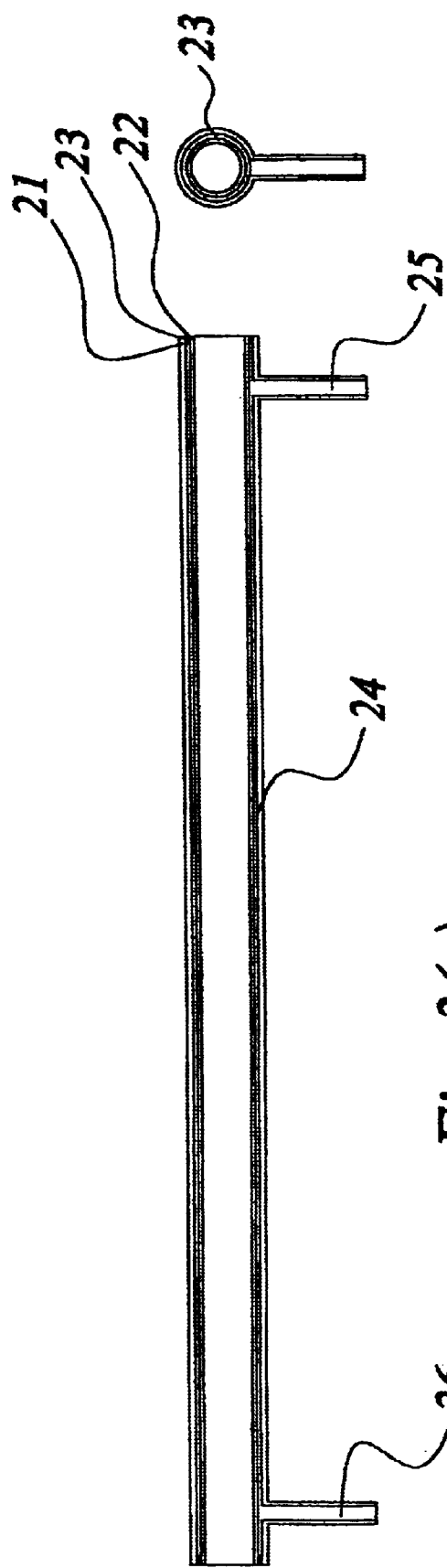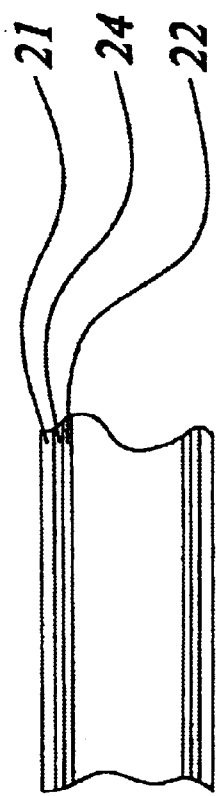
Fig. 3(a)
Fig. 3(b)

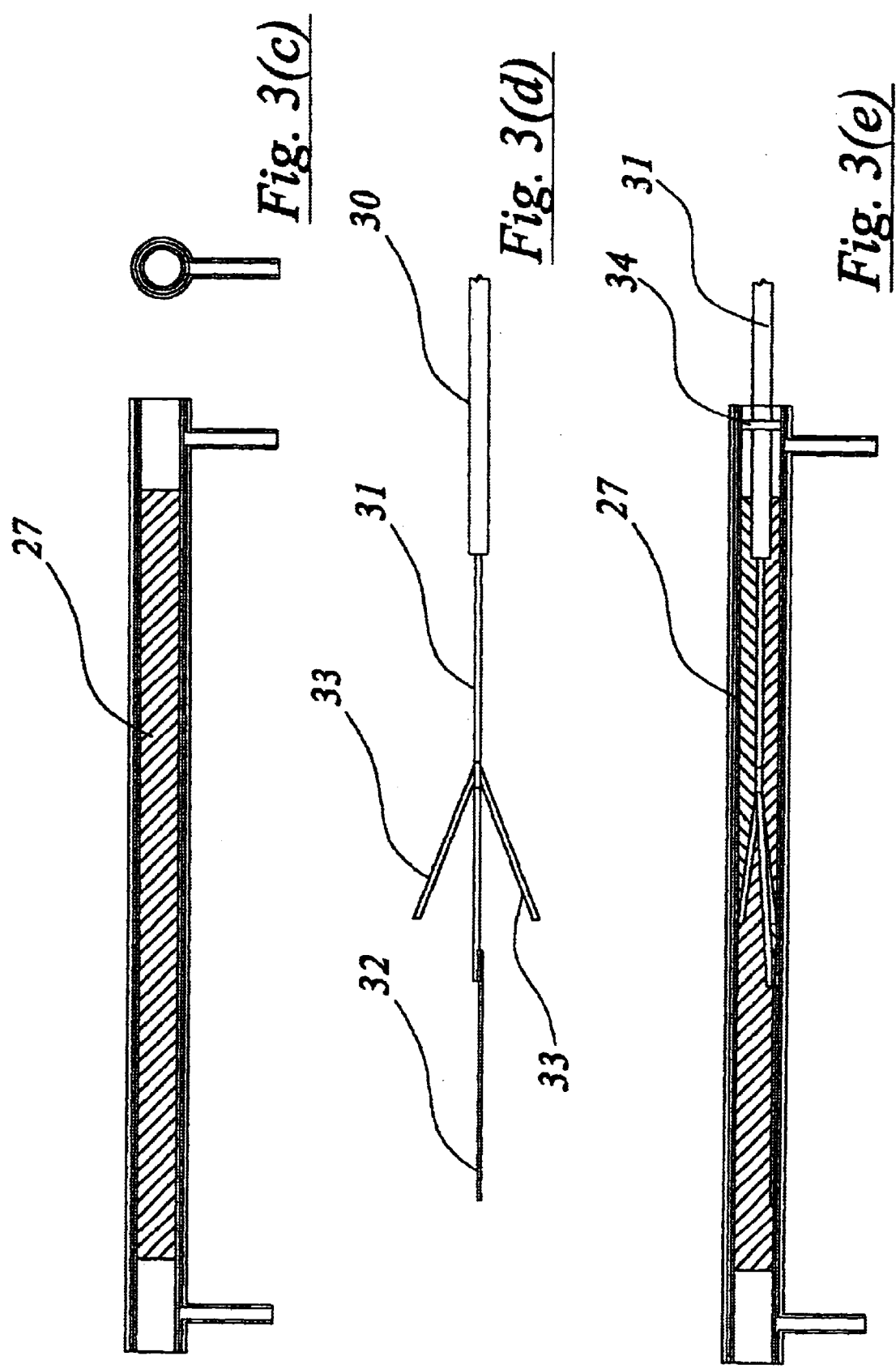

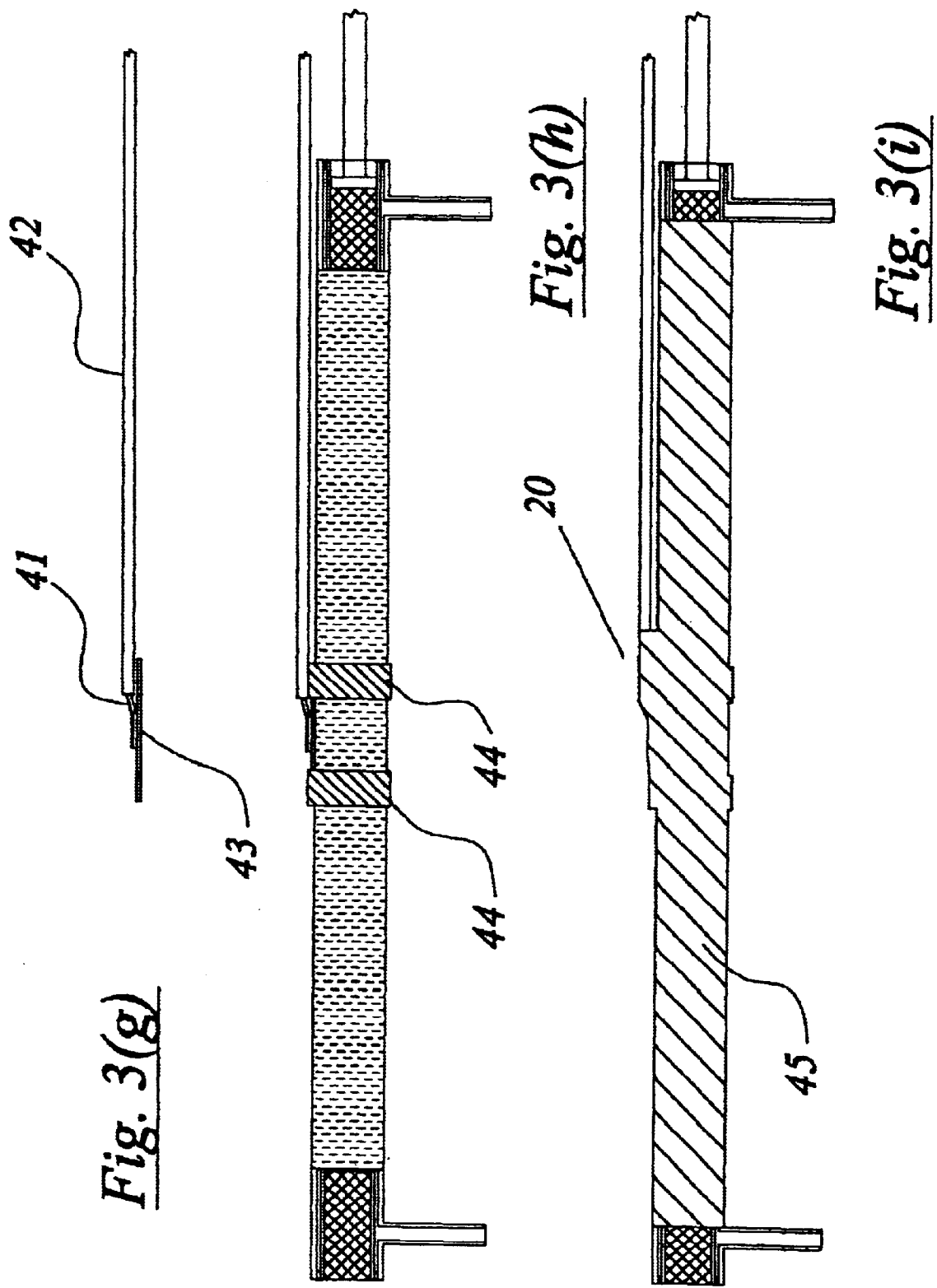

METHOD AND APPARATUS FOR THE ANALYSIS OF A LIQUID CARRYING A SUSPENSION OF ORGANIC MATTER

BACKGROUND OF THE INVENTION

1. Field of the Invention

The present invention relates to a method and apparatus for the analysis of a liquid carrying a suspension of organic matter. The invention is particularly directed towards an ozone hydroxyl radical analysis method of the type utilising ozone and generally comprising the steps of:

sampling the liquid;

delivering the sample to the reactor vessel;

adding an acid to lower the pH;

stripping off inorganic carbon as carbon dioxide to give a value for total inorganic carbon present;

using a base liquid having hydroxyl ions to increase the pH;

adding ozone through a reactor inlet to form hydroxyl radicals and thus ensure effective oxidation;

cutting off the ozone;

lowering the pH of the sample; and stripping off carbon dioxide to give a value of total organic carbon present.

2. Background Information

Ideally any analyser should be able to sequentially analyse samples from a number of different location.

Preferably any such analyser should be able to measure total organic carbon, total inorganic carbon, total carbon and after correlation, chemical oxygen demand (COD) and biochemical oxygen demand (BOD).

As mentioned above, the analysers of the type which the present invention is concerned, is to use the principle that ozone can be used to produce free hydroxyl radicals. The radicals will oxidise the organic material they come in contact with and produce carbon dioxide. When the pH is lowered, the gas is stripped off with oxygen or any other stripping gas such as air which does not itself contain carbon dioxide e.g. air nitrogen, etc. and the amount of carbon dioxide is measured with a carbon dioxide detector. Then a clear measure of total organic carbon is obtained.

Any analyser should have low chemical usage costs and a good oxidation of both dissolved organic material and particulates. Efficient ozone generation is vital.

It is also essential that good control devices be used to ensure that the system operates correctly.

Objects

The present invention is directed towards providing an improvement in such an analysis method and to provide an improved construction of reactor vessel and apparatus for carrying out such a method and in particular to providing an improved construction of ozone generator.

SUMMARY OF THE INVENTION

According to the invention there is provided an ozone hydroxyl radical analysis method for a liquid carrying a suspension of organic matter of the type utilising ozone in an analyser including a reactor vessel and a plurality of fluid inlet and outlet valves comprising the steps of:

sampling the liquid;

delivering the sample to the reactor vessel;

adding an acid to lower the pH;

stripping off inorganic carbon as carbon dioxide to give a value for total inorganic carbon present;

using a base liquid having hydroxyl ions to increase the pH;

adding ozone through a reactor inlet to from hydroxy radicals and thus ensure effective oxidation;

cutting off the ozone;

lowering the pH of the sample; and stripping off carbon dioxide to give a value of total organic carbon present, and;

prior to carrying out the method the initial stop is performed of:

introducing beads of an inert material into the reactor vessel; and periodically the step is performed of introducing a metallic catalyst into the reactor vessel to coat the beads.

The use of beads of an inert material has been found to be particularly effective when combined with a metallic catalyst.

Ideally the catalyst is introduced into the reactor vessel each time a liquid sample is delivered into the reactor vessel. Particularly suitable forms of metallic catalysts are manganese, cobalt, nickel, silver, lead and molybdenum.

Ideally the beads are glass beads and the catalyst is manganese. The beads are substantially spherical having a diameter of between 1 mm and 10 mm and more preferably between 2.5 mm and 3.5 mm.

The ozone concentration can be between 1% and 25% by volume and is generally greater than 8% by volume.

The base liquid is a concentrated Source of hydroxy ions of between 0.25 and 10 molar, generally greater than 1 molar and preferably greater than 1.2 molar and the base liquid is chosen from sodium hydroxide or potassium hydroxide.

Ideally the sample, acid, base liquid and ozone mixture are recirculated through the reactor vessel and ideally the inlet used to deliver ozone into the reactor vessel is washed periodically by an acid and this acid is often that used to lower the pH.

Ideally in each reaction is carried out an initial detection step is carried out to ascertain if carbon dioxide gas is given off and in the event of the level of carbon dioxide detected falling below a pre-set level, the test is abandoned until the malfunction is corrected.

In this latter method the pre-set level is determined by introducing the acid and base liquid into the reactor vessel and measuring the resultant carbon dioxide released.

In a method according to the invention when the total inorganic carbon is being detected the test is continued until the flow of carbon dioxide ceases.

Further an automatic leak test is performed periodically by:

closing all outlet valves from the reactor vessel;

delivering a gas into the reactor vessel at a fixed rate; and monitoring the flow of oxygen.

Additionally an automatic blockage test is performed by closing off all the valves except for the valve or valves in one gas path through the reactor vessel and delivering a gas at a pre-set flow rate and pressure through said gas path and monitoring the gas throughput.

Further the invention provides an ozone hydroxyl radical analyser of the type comprising:

a reactor vessel having inlets and outlets;

a sampling device connected to the reactor vessel;

a base liquid tank connected to the reactor vessel;

an acid tank connected to the reactor vessel;

an ozone generator feeding the reactor vessel;

associated pumps and valves;

a control and measurement unit; and the reactor vessel includes a plurality of beads of an inert material.

In one embodiment of the invention the inert material is glass.

The beads are substantially spherical having a diameter of between 1 mm and 10 mm and preferably between 2.5 mm and 3.5 mm.

In one embodiment the ozone generator and the acid tank feed a common inlet to the reactor vessel.

The reactor vessel is constructed so that it has a liquid outlet at its lowermost position and in which all sources of the reactor vessel slope downwards to the liquid outlet to ensure the smooth flow of liquid out of the reactor vessel.

Preferably the reactor vessel is formed from a weldable fluorocarbon which can be chosen from perfluoroalkoxy (PFA), polyvinylidine fluoride (PVDF) and fluorinated ethylene propylene (FEP).

A particularly preferable construction of ozone generator is of concentric tube type wherein the inner and outer walls of the tube form an annular gap through which oxygen containing gas flows between an outer tubular electrode and an inner tubular electrode which is applied to the innermost surface, the interior of the tube being filled with a sealant.

Preferably the sealant is silicon rubber.

An ideal construction of ozone generator is one manufactured from a leaded glass.

BRIEF DESCRIPTION OF THE DRAWINGS

The invention will be more dearly understood from the following description of some embodiments thereof, given by way of example only describe with reference to the accompanying drawings in which:

FIG. 3(a) to (i) illustrates an ozone generator according to the invention in various stages of manufacture;

DESCRIPTION OF PREFERRED EMBODIMENTS

Figure 1:
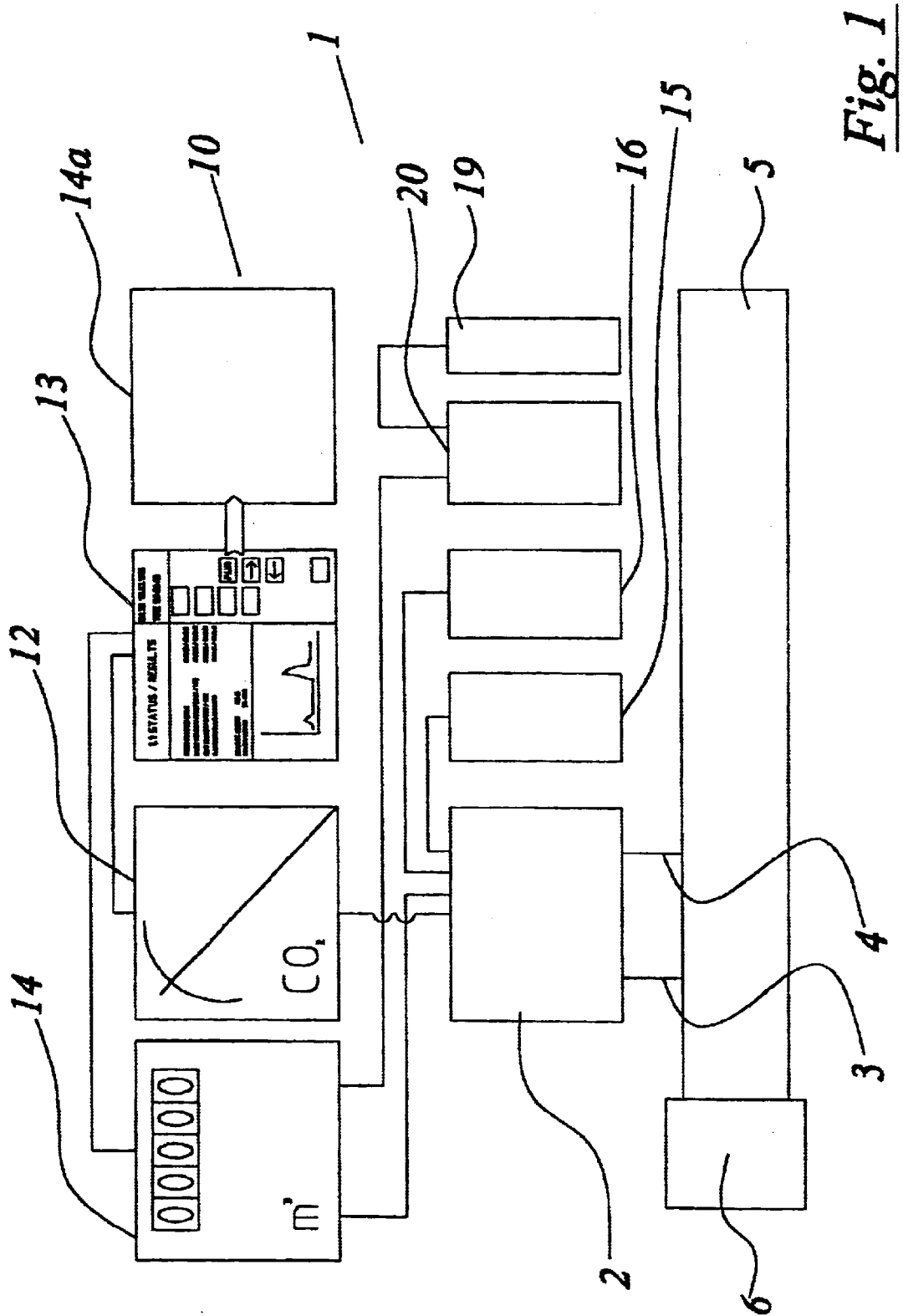
FIG. 1 is a schematic view of an analyser according to the invention.
Figure 2:
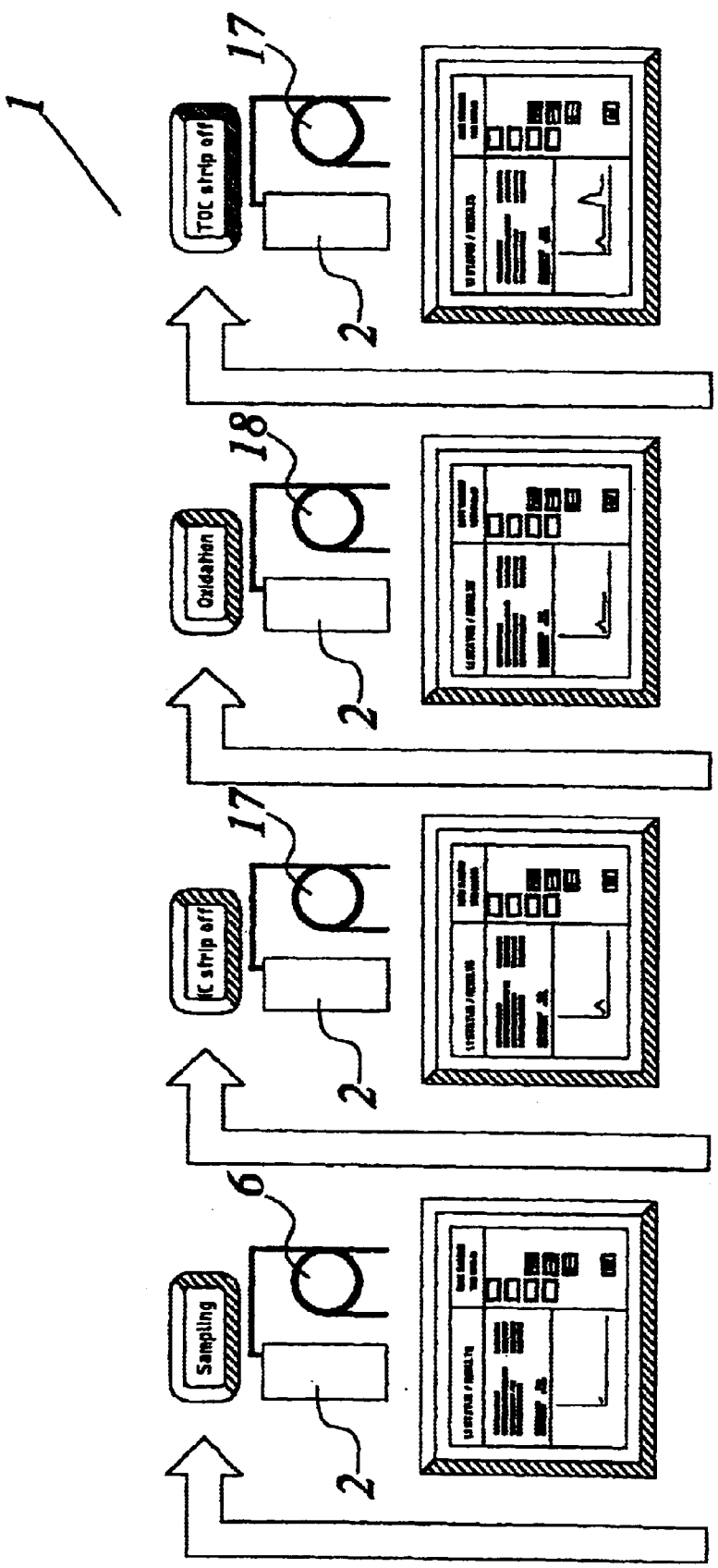
FIG. 2 is a schematic view showing the principle of operation of the analyser.
Figure 3F:
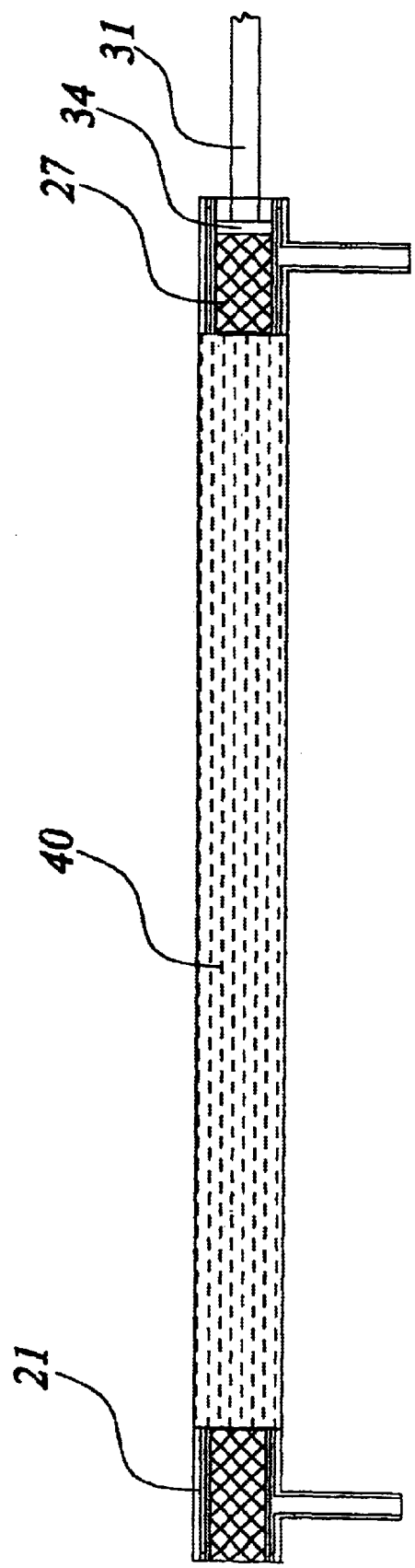

Referring to the drawings and initially to FIGS. 1 and 2, essentially the analyser comprises three separate units, namely the ozone generator, the actual reaction or reactor vessel itself and the processing control equipment. The processing control equipment incorporates a microprocessor and ideally it has a membrane keypad.

Referring now to FIG. 1, the analyser is indicated generally by the reference numeral 1 and comprises a reactor vessel 2 having sample inlets and outlets 3 and 4 respectively for a liquid stream identified by the reference numeral 5. The sample is obtained by a sample pump 6. The reactor vessel 2 is connected to a control and measurement unit indicated generally by the reference numeral 10 which is diagrammatically represented by a $CO_2$ meter 12, an LCD screen 13, printer 14a and a mass flow controller 14. The printer 14a is an optional piece of equipment. The reactor vessel 2 is fed from an acid tank or vessel 15 and a base liquid tank or vessel 16. Suitable pumps, not shown in FIG. 1, but identified by the reference numerals 17 and 18 respectively in FIG. 2, are used. An oxygen storage tank 19 is illustrated feeding an ozone generator 20 which in turn feeds the reactor vessel 2. The oxygen storage tank 19 also feeds the reactor vessel 2 directly.

Figure 4:
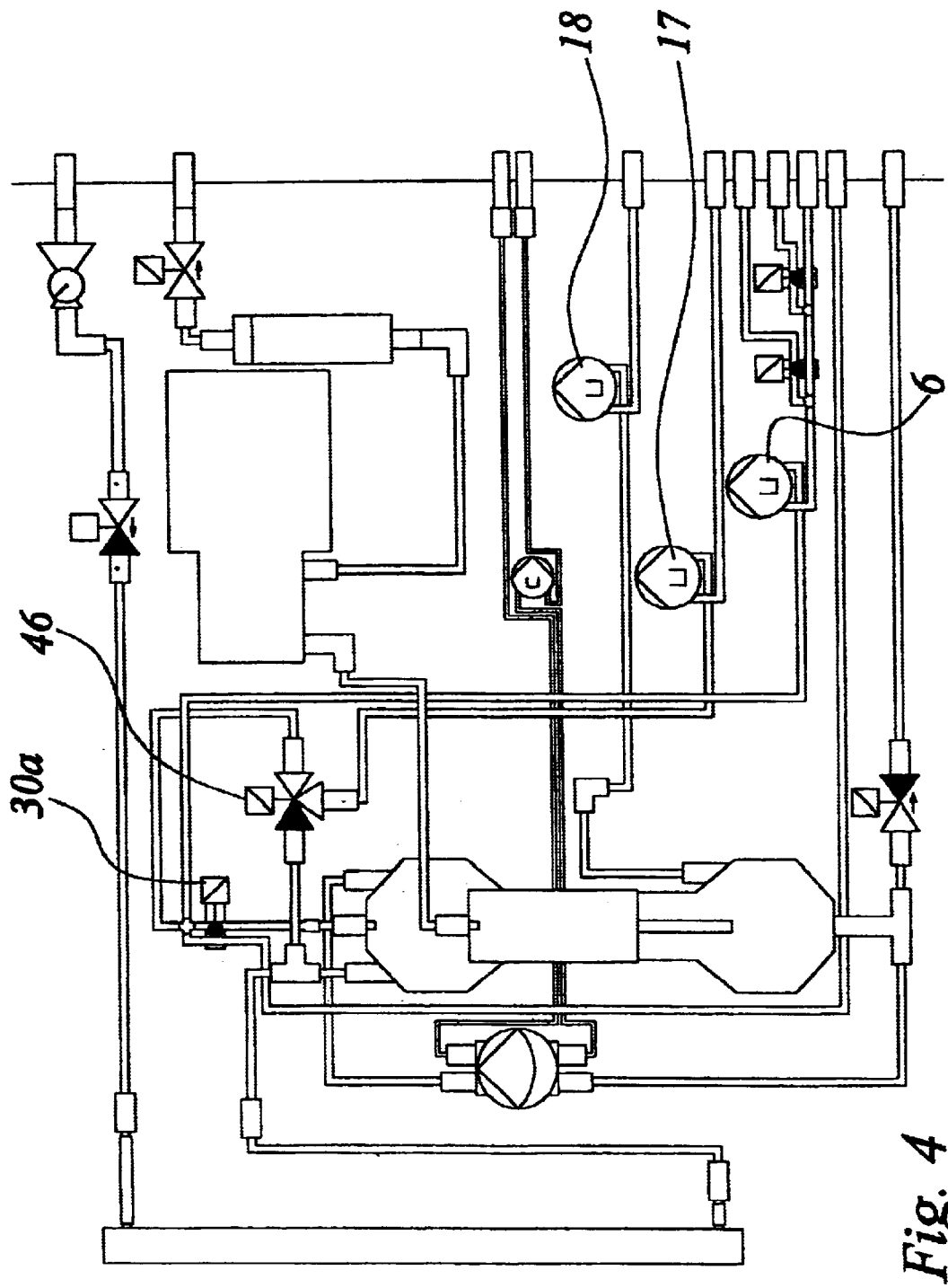
FIG. 4 illustrates the standard form of sample analysis layout.
Figure 5:
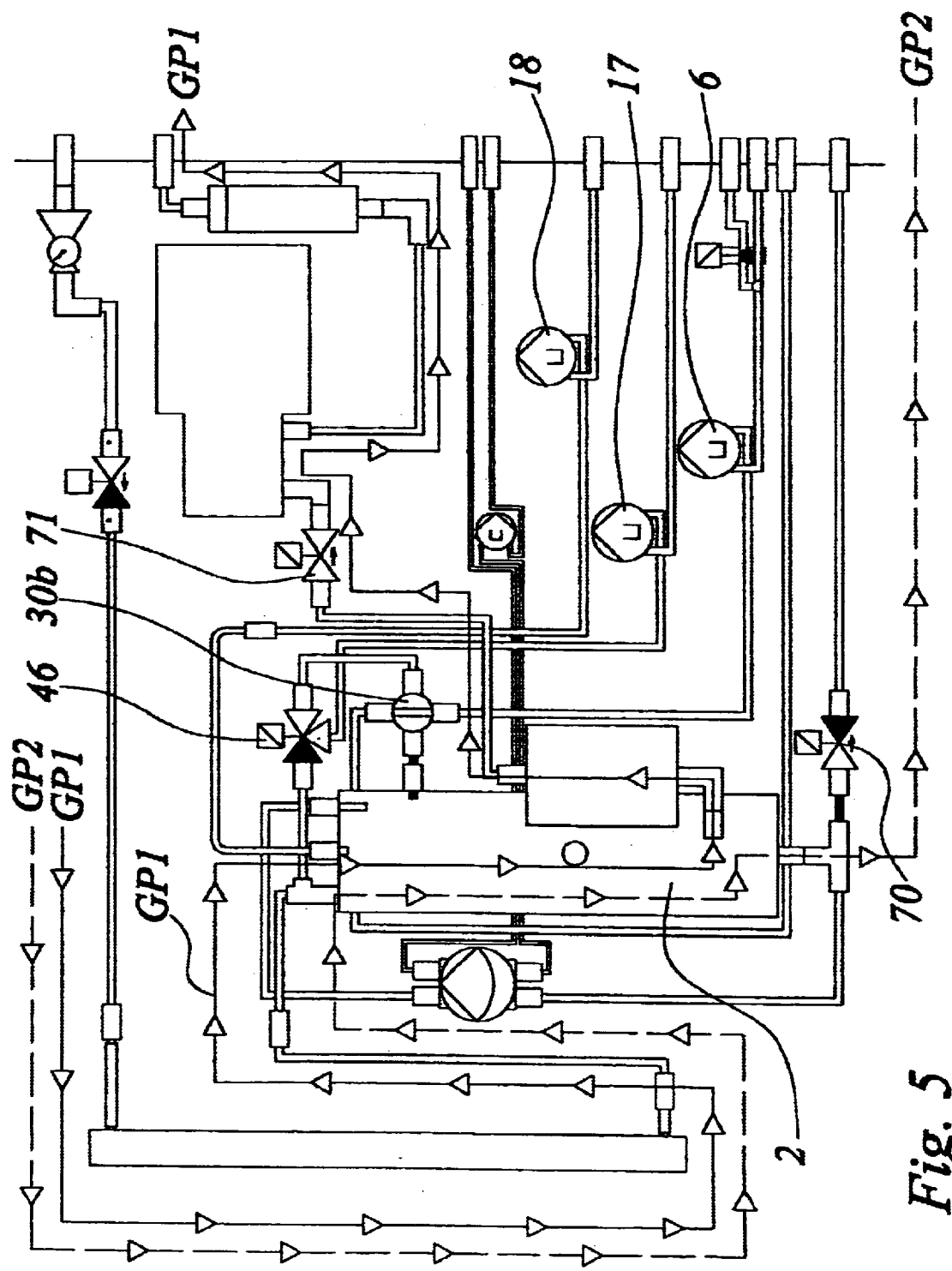
FIG. 5 shows the high range form of sample analysis layout with the cleaning valve in position.

Referring now to FIG. 2 the principle of the operation of the analyser can be easily seen. More detailed comments on specific features of the present invention are dealt with below. It is however advantageous to describe the method in broad outline. In the first stage there is sampling with no filtration and when a representative sample from the liquid stream 5 is to be analysed is pumped into the analyser 1, the sample bypasses the reactor vessel 2 until it is certain that there is only a new sample of water contained in the system, then a valve at the top of the analyser, not shown in all the drawings, but identified by the reference numerals 30(a) in FIG. 4 and 30(b) in FIG. 5, is opened to allow the correct sample volume to enter the reactor vessel 2. The valve is then closed. In stage 2 acid, in the present embodiment, 1.8N Sulphuric Acid ($H_2SO_4$) is delivered by the pump 17 into the reactor vessel 2 through the same valve. This lowers the pH to less than 2 and inorganic carbon is stripped off by oxygen and analysed. The base pump 18 is then operated to deliver 1.2N Sodium Hydroxide (NaOH) to the reactor vessel 2. This increases the pH to greater than 12. Then the ozone generator 20 is switched on to generate ozone used in the region. With both the ozone and sodium hydroxide hydroxyl radicals are formed and effective oxidation takes place.

Figure 6:
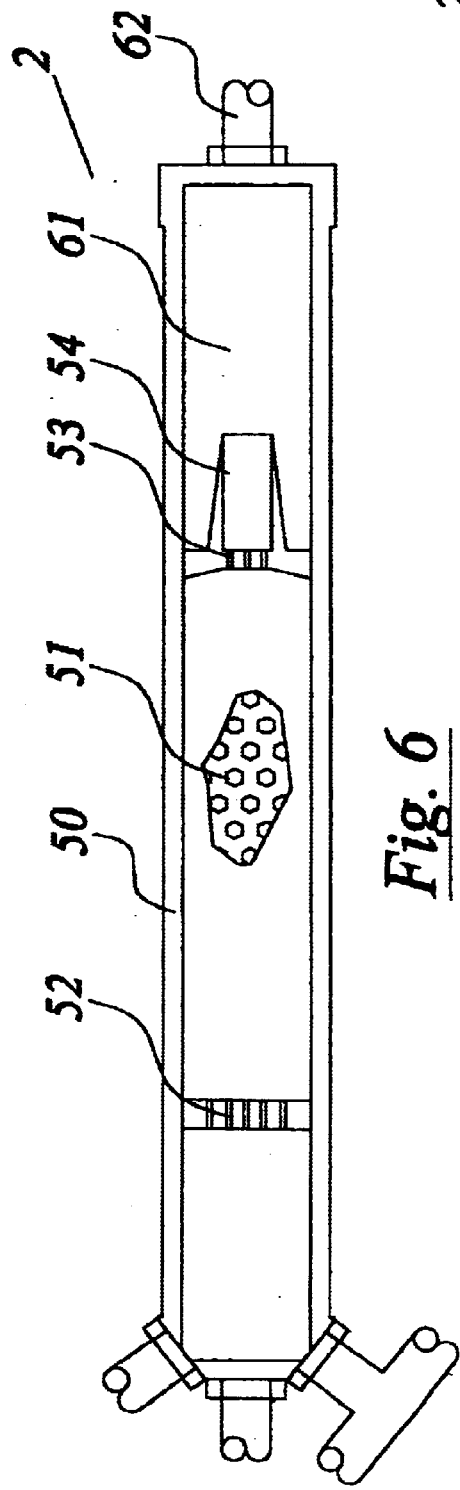
FIG. 6 is a diagrammatic part sectional view with sectional lines omitted of a reactor vessel according to the invention.
Figure 7:
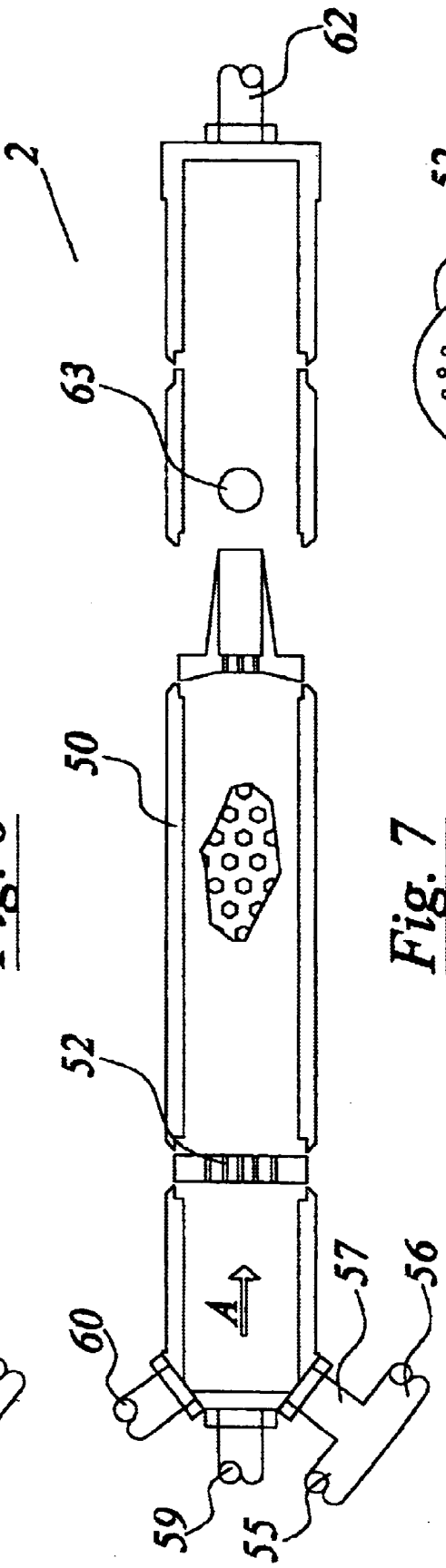
FIG. 7 is an exploded view of the reactor vessel as illustrated in FIG. 6.

Referring again to FIGS. 4 and 5, it will be noted that the valve 46 can be used to wash the ozone inlet. The valve 46 works by directing the acid used in the process via the ozone inlet through the reactor 2. This is also illustrated in FIGS. 6 and 7 as described below. The oxygen as shown in FIGS. 4 and 6 passes from the oxygen storage tank 19 through the mass flow controller 14 into the ozone generator 20 and then into the reactor vessel 2 and not as shown diagrammatically in FIG. 1

A sampling device is provided by the valve 30(b) is a ball valve which is used as it provides a defined sample quantity. This can be seen clearly in FIG. 5.

Finally in stage 4 when the sample has been completely oxdised, the ozone generator is switched off and the pH of the sample is lowered again by delivering acid from the acid vessel 15 by the pump 17 to the reactor vessel 2. The carbon dioxide is then stripped off by oxygen and is monitored by the control system.

The carbon monitoring is carried out by a suitable IR system detector incorporated in the control and measurement unit 10.

Referring now to FIG. 3(a) to (i), there is illustrated the ozone generator in various stages of manufacture. The ozone generator 20 is only shown fully assembled in FIG. 3(i).

Referring to FIG. 3(a) and (b) the ozone generator 20 comprises a doublwalled tube formed from an outer wall 21, an inner wall 22 having annular end seals 23 to form an annular space 24 therebetween. The end seals 23 and the outer and inner walls 21 and 22 are all manufactured from the one glass ideally leaded glass. There is provided an inlet 25 and an outlet 26 for the annular space or gap 24. FIG. 3(b) which is an enlarged view of portion of FIG. 3(a) shows the annular space 24 more clearly.

Mounted on the interior of the inner tube 22 is a copper foil 27 as illustrated in FIG. 3(c). The copper foil 27 has to be fitted to the inner tube 22 in such a way as to ensure that there are no air bubbles between the copper foil 27 and the glass 22. The copper foil 27 forms one of the anodes of the ozone generator 20. A high voltage cable 30 having an inner copper conductor 31 has a length of copper foil 32 secured thereto as well as two support legs 33. The copper foil 32 is secured by adhesive to the other copper foil 27 and a grommet 34 holds the cable in position. see FIG. 3(e).

A packing material such as silicone rubber is then filled into the inner tube 22 to secure the copper foil 27 and me high voltage cable 30 securely in position. When the silicone rubber is hardened the second anode in the form of an aluminum foil 40 (see FIG. 3)) is secured to the outer tube 21, A suitable neural connector formed from a cable 41 with insulation 42 is connected to a strip of copper foil 43 which is secured to the aluminum foil 40 by adhesive and two further bands of copper foil 44 (see FIG. 3(g) and 3(h)). The whole assembly is then wrapped in a suitable material 45 such as, for example, any tape sold under the Trade Mark 3M Scotch Super 33+ Vinyl Electrical Tape.

Figure 8:
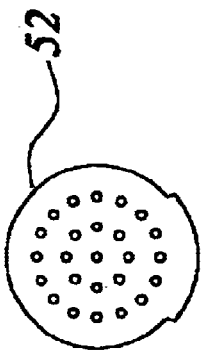
FIG. 8 is a end view in the direction of the arrow A in FIG. 7.

Referring to FIGS. 6 to 8 inclusive there is illustrated the reactor vessel 2 comprising a main body 50 separated into an intermediate compartment carrying a plurality of glass beads 51 between an upper grid 52 and a lower grid 53 mounted in a discharge nozzle 54. The reactor vessel 2 is illustrated lying on its side, but normally it would be mounted vertically. The reactor vessel 2 has an acid inlet pipe 55 and an ozone inlet pipe 56 feeding a common inlet 57. A sample inlet 59 is illustrated as is a base liquid inlet 60. A further inlet for a circulation pump, not shown, is mounted behind the sample inlet 59. The upper grid 52 is illustrated in more detail in FIG. 8 and simply comprises a plate having a plurality of holes, whose diameter is less than that of the glass beads. The grid 53 is similarly constructed. The nozzle 54 feeds a lower chamber 61 having a liquid discharge outlet pipe 62 which is connected by a pump, not shown, to recirculate the liquid back through the further inlet. A gas outlet 63 is mounted in the lower chamber 61 and is connected to the carbon dioxide analyser 12. As the carbon dioxide and ozone comes out of solution it is delivered to the carbon dioxide analyser and the test continues to be performed until no more or a minimal amount of carbon dioxide is detected.

In use, the liquid sample will be recirculated from the outlet pipe 62 back through the further inlet and when ozone is being generated, the sample will contain a certain amount of ozone which will be recirculated.

In operation, generally a cast will be introduced into the reactor vessel 2 each time a sample is being analysed. The catalyst is advantageously chosen from manganese, cobalt, nickel, silver, lead and molybdenum. It has been found that with the glass beads it manganese is introduced the base liquid causes the manganese mixed with the sodium hydroxide and acid to coat the glass beads. This is thus retained in the reactor vessel 2 Aternatively, it can be introduced over longer periods.

Ideally the reactor vessel 2 is manufactured from a weldable fluorocarbon such as perfluoroalkoxy (PFA), polyvinylidine fluoride (PVDF) and fluorinated ethylene propylene (FEP). There may be other similar materials which may be useful. The great advantage of using a weavable fluorocarbon is that it is relatively easy to manufacture the reactor vessel. Ordinary plastic materials cannot be used as the hydroxyl radicals will oxidise them.

It is envisaged that beads of other inert materials such as comics could be used and it is envisaged hat certain of the cat would react suitably depending on the base liquids used which will generally either be sodium hydroxide or potassium hydroxide.

The beads have been found to be particularly useful when produced in sizes between 2.5 mm and 35 mm diameter, but it is engaged Matthe beads could be as small as 1 mm in diameter or indeed as large as 10 mm, though it has been found that the smaller beads are preferable as they provide very good mixing of the ozone and the liquid together with very good retention of the catalyst in the reactor vessel.

It is envisaged that the ozone concentration will generally be between 5% and 25% by volume and it is preferably that it over at least 8% by volume though it can be as low as 1%.

Ideally the base liquid is a concentrated source of hydroxyl ions of between 0.25 and 10 molar, but should generally be greater than 1 molar. We have found that when sodium hydroxide is used that the base liquid greater than 1.2 molar is very useful.

Further as can be seen and is referred to above in relation to the valve 46, the acid inlet pipe 55 and the ozone inlet pipe 56 feed a common inlet 57 and thus if there is any residue which is often the case left by the ozone in Me common inlet pipe 57 to the reactor vessel 2 which could cause clogging, the acid from the acid inlet pipes 55 will wash the common inlet 57 and thus prevent a built-up of contaminants.

The control system 10 and in particular using the mass flow controller 14 allows various tests to be performed during the analysis to prevent the incidence of malfunction. In the method according to the invention when each reaction or analysis is being carried out an initial detection step is carried out to ascertain if carbon dioxide gas is given off. Since all base liquids of their nature will carry a certain amount of carbon dioxide if there is no carbon dioxide detected, or if indeed the level of carbon dioxide detected is minimal, namely falling below some pre-set level, then the test is abandoned until the malfunction is corrected. Further to avoid the possibility that the detection of inorganic carbon is terminated before all the inorganic carbon has been stripped off, which in turn would ensure that the detection of organic carbon was incorrect in the next phase of the analysis the method is such that while the total inorganic carbon is being detected, the test is continued until the flow of carbon dioxide effectively ceases.

According to the present invention there is provided a method to ensure that the level of carbon dioxide dissolved in the base solution can be quickly measured, or that any correction can be made. This can be measured without oxidation and is performed quickly during the reaction process. Thus a pre-set level of carbon dioxide can be obtained by introducing the acid and the base liquid and measuring the carbon dioxide given off. This also ensures that the value of total inorganic carbon is not overstated and the amount of carbon dioxide thus detected can be subtracted from the actual amount detected to obtain a net value of carbon dioxide.

Further an automatic leak test is performed by closing all the outlet valves from the reactor vessel and delivering a gas obviously in this case oxygen through the reactor vessel at a fixed rate and monitoring the flow of the oxygen, if the flow of oxygen does not stop then the leak is immediately detected as the pressure of the oxygen should not reduce. The great advantage of this automatic leak test is that by injecting oxygen at an elevated pressure, it is possible to detect fluid leaks at an early stage in the analyser. Thus, it allows leaks to be detected when the leak is at an early stage of development. This can be very important as an ozone is a to gas and there is thus safety implications in avoiding all leaks. This is particularly the case where ozone is used in an area such as in the present invention and is not a major component in any production operation. This can be particular advantageous as the analyser may operate unattended for considerably long periods.

Further, tests are performed to ascertain whether there is any blockage in the system. It will be appreciated from the description above that there is more than one gas path through the reactor vessel. For example, that of ozone, that of oxygen to the ozone generator and then to the reactor vessel that of the ozone directly to the rector vessel and so on. To again ascertain blockage, all the valves are closed off except the valve or valves in one gas path through the reactor vessel and then a gas is delivered usually oxygen at a pre-set flow rat and pressure through said gas path and then the gas throughput is monitored. Again if the flow is too low, then a blockage is detected and the malfunction noted and the analyser shut down. The gas paths are shown in FIG. 5 the first gas path is shown by the arrows and the full line and identified by the letters GP1 and the second gas path is shown by the interrupted lines and by the identification GP2. For the first gas path, namely GP1, the valve identified by the reference number 70 is dosed and for the second gas path GP2 the valve identified by the reference numeral 71 is closed.

It will be appreciated that the control system can be so arranged as to carry out these tests automatically at fixed periods of time, or after the analyser has been operated for a pre-set time. The intervals can be chosen by the operators as they deem fit and further the operator can, as it will be appreciated, be allowed to operate such tests manually.

In accordance with the invention, the analyser normally uses sulphuric acid, but in certain circumstances it may be more advantageous to use other acids, such as hydrochloric acid. The problem with hydrochloric acid is it cannot be used with ozone and a stainless steel reaction vessel due to its extreme corrosive properties when mixed with it.

It has been found very important to ensure that there is a good concentration of ozone and thus it is vital that the ozone generator be efficient. Further, it has been found that the use of the catalyst greatly improves the effectiveness of the reactor vessel and further the recirculation of the sample through the reactor vessel facilitates the production of ozone and base and thus a more accurate analysis.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to the embodiment hereinbefore described, but may be varied in both construction and detail.

What is claimed is:

1. A total organic carbon analysis method for a liquid carrying a suspension of organic matter utilizing ozone and hydroxyl radicals in an analyser including a reactor vessel and a plurality of fluid inlet and outlet valves comprising;

introducing beads of an inert material into the reactor vessel;

sampling the liquid;

delivering the sample to the reactor vessel;

adding an acid to lower the pH of the liquid;

stripping off inorganic carbon as carbon dioxide and measuring carbon dioxide to give a value for total inorganic carbon present;

adding a base liquid having hydroxyl ions to increase the pH of the liquid;

adding ozone through a reactor inlet to form hydroxyl radicals and oxidize organic material in the liquid to carbon dioxide;

cutting off the ozone;

lowering the pH of the sample;

stripping off carbon dioxide and measuring carbon dioxide to give a value of total organic carbon present; and periodically introducing a metallic catalyst into the reactor vessel to coat the beads.

2. A method as claimed in claim 1 in which the metallic catalyst is chosen from one or more of manganese, cobalt, nickel, silver, lead and molybdenum.

3. A method as claimed in claim 1 in which the beads are glass beads and the catalyst is manganese.

4. A method as claimed in claim 3 in which the ozone concentration is between 1% and 25% by volume.

5. A method as claimed in claim 3 in which the ozone concentration is greater than 8% by volume.

6. A method as claimed in claim 3 in which the base liquid is a concentrated source of hydroxyl ions between 0.25 and 10 molar.

7. A method as claimed in claim 3 in which the base liquid is a concentrated source of hydroxyl ions greater than 1.0 molar.

8. A method as claimed in claim 3 in which the bass liquid is a concentrated source of hydroxyl ions greater than 1.2 molar.

9. A method as claimed in claim 3 in which the liquid is chosen from sodium hydroxide or potassium hydroxide.

10. A method as claimed in claim 3 in which the sample, acid, base liquid and ozone mixture are recirculated through the reactor vessel.

11. A method as claimed in claim 3 in which the inlet used to deliver ozone into the reactor vessel is washed periodically by an acid.

12. A method as claimed in claim 3 in which the inlet used to deliver ozone into the reactor vessel is washed periodically by the acid used to lower the pH.

13. A method as claimed in claim 3 in which as each reaction is carried out an initial detection step is carried out to ascertain if carbon dioxide gas is given off and in the event of the level of carbon dioxide detected falling below a pre-set level, the test is abandoned until the malfunction is corrected.

14. A method as claimed in claim 3 in which as each reaction is carried out an initial detection step is carried out to ascertain if carbon dioxide gas is given off and if it falls below a pre-set level determined by measuring the carbon dioxide gas given off by the acid reacting with the base liquid alone in the reactor vessel the test is abandoned until the malfunction is detected.

15. A method as claimed in claim 3 in which the initial measuring step is carried out by measuring the carbon dioxide gas given off by the acid reacting with the base liquid alone in the reactor vessel to adjust the value for the total inorganic carbon.

16. A method as claimed in claim 3 in which when the total inorganic carbon is being detected the test is continued until the flow of carbon dioxide ceases.

17. A method as claimed in claim 3 in which an automatic leak test is performed periodically by:
   closing all outlet valves from the reactor vessel;
   delivering oxygen into the reactor vessel at a fixed rate; and
   monitoring the flow of oxygen.

18. A method as claimed in claim 3 in which an automatic blockage test is performed by closing off all the valves except for the valve or valves in one gas path through the reactor vessel and delivering a gas at a pre-set flow rate and pressure through said gas path and monitoring the gas throughput.

19. A method as claimed in claim 1 in which the ozone concentration is greater than 8% by volume.

20. A method as claimed in claim 19 in which the base liquid is a concentrated source of hydroxyl ions greater than 1.2 molar.

21. A method as claimed in claim 19 in which the base liquid is chosen from sodium hydroxide or potassium hydroxide.

22. A method as claimed in claim 1 in which the sample and ozone are recirculated through the reactor vessel.

23. A method as claimed in claim 22 in which the ozone concentration is greater than 8% by volume.

24. A method as claimed in claim 22 in which the bass liquid is a concentrated source of hydroxyl ions greater than 1.2 molar.

25. A method as claimed in claim 22 in which the be liquid is chosen from sodium hydroxide or potassium hydroxide.

26. A method as claimed in claim 1 in which the inlet used to deliver ozone into the reactor vessel is washed periodically by an acid.

27. A method as claimed in claim 26 in which the ozone concentration is greater than 8% by volume.

28. A method as claimed in claim 26 in which the base liquid is a concentrated source of hydroxyl ions greater than 1.2 molar.

29. A method as claimed in claim 26 in which base liquid is chosen from sodium hydroxide or potassium hydroxide.

30. A method as claimed in claim 26 in which the sample, acid, base liquid and ozone mixture are recirculated through the reactor vessel.

31. A total organic carbon analysis method for a liquid carrying a suspension of organic matter utilizing ozone and hydroxyl radicals in an analyser including a reactor vessel and a plurality of fluid inlet and outlet valves comprising;
   introducing beads of an inert material into the reactor vessel;
   sampling the liquid;
   delivering the sample to the reactor vessel;
   adding an acid to lower the pH of the liquid;
   adding a metallic catalyst to coat the beads;
   stripping off inorganic carbon as carbon dioxide and measuring carbon dioxide to give a value for total inorganic carbon present;
   adding a base liquid having hydroxyl ions to increase the pH of the liquid;
   adding ozone through a reactor inlet to form hydroxyl radicals oxidize organic material in the liquid to carbon dioxide;
   cutting off the ozone;
   lowering the pH of the sample; and
   stripping off carbon dioxide and measuring carbon dioxide to give a value of total organic carbon present.

32. A method as claimed in claim 31 in which the metallic catalyst is chosen from one or more of manganese, cobalt, nickel, silver, lead and molybdenum.

33. A method as claimed in claim 31 in which the beads are glass beads and the catalyst is manganese.

34. A method as claimed in claim 33 in which the ozone concentration is greater than 8% by volume.

35. A method as claimed in claim 33 in which the base liquid is a concentrated source of hydroxyl ions greater than 1.2 molar.

36. A method as claimed in claim 33 in which the sample, acid, base liquid and ozone mixture are recirculated through the reactor vessel.

37. A method as claimed in claim 33 in which the inlet used to deliver ozone into the reactor vessel is washed periodically by an acid.

38. A method as claimed in claim 33 in which as each reaction is carried out an initial detection step is carried out to ascertain if carbon dioxide gas is given off and in the event of the level of carbon dioxide detected falling below a pre-set level, the test is abandoned until the malfunction is corrected.

39. A method as claimed in claim 33 in which as each reaction is carried out an initial detection step is carried out to ascertain if carbon dioxide gas is given off and if it falls below a pre-set level determined by measuring the carbon dioxide gas given off by the acid reacting with the base liquid alone in the reactor vessel the test is abandoned until the malfunction is detected.

40. A method as claimed in claim 33 in which the initial measuring step is carried out by measuring the carbon dioxide gas given off by the acid reacting with the base liquid alone in the reactor vessel to adjust the value for the total inorganic carbon.

41. A method as claimed in claim 33 in which when the total inorganic carbon is being detected the test is continued until the flow of carbon dioxide ceases.

42. A method as claimed in claim 33 in which an automatic leak test is performed periodically by:
   closing all outlet valves from the reactor vessel;
   delivering oxygen into the reactor vessel at a fixed rate; and
   monitoring the flow of oxygen.

43. A method as claimed in claim 33 in which an automatic blockage test is performed by closing off all the valves except for the valve or valves in one gas path through the reactor vessel and delivering a gas at a pre-set flow rate and pressure through said gas path and monitoring the gas throughput.

* * * * *